(12) United States Patent
Pantelidis et al.

(10) Patent No.: US 7,981,441 B2
(45) Date of Patent: Jul. 19, 2011

(54) DRUG DELIVERY SYSTEMS USING MESOPOROUS OXIDE FILMS

(75) Inventors: Dimitrios Pantelidis, Menlo Park, CA (US); John C. Bravman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1350 days.

(21) Appl. No.: 10/597,938

(22) PCT Filed: Dec. 1, 2004

(86) PCT No.: PCT/US2004/040270
§ 371 (c)(1),
(2), (4) Date: Aug. 11, 2006

(87) PCT Pub. No.: WO2005/082277
PCT Pub. Date: Sep. 9, 2005

(65) Prior Publication Data
US 2007/0160639 A1    Jul. 12, 2007

Related U.S. Application Data

(60) Provisional application No. 60/546,091, filed on Feb. 18, 2004.

(51) Int. Cl.
*A61F 2/02* (2006.01)
(52) U.S. Cl. .................................................... 424/423
(58) Field of Classification Search .................. None
See application file for complete search history.

(56) References Cited

U.S. PATENT DOCUMENTS

| | | | |
|---|---|---|---|
| 5,057,296 | A | 10/1991 | Beck |
| 5,102,643 | A | 4/1992 | Kresge et al. |
| 5,516,781 | A | 5/1996 | Morris et al. |
| 5,622,684 | A | 4/1997 | Pinnavaia et al. |
| 6,054,111 | A | 4/2000 | Antonietti et al. |
| 6,318,124 | B1 | 11/2001 | Rutherford et al. |
| 6,334,988 | B1 | 1/2002 | Gallis et al. |
| 6,365,266 | B1 | 4/2002 | MacDougall et al. |
| 6,395,299 | B1 | 5/2002 | Babich et al. |
| 6,458,310 | B1 | 10/2002 | Liu |
| 6,465,365 | B1 | 10/2002 | Annapragada |
| 6,511,658 | B2 | 1/2003 | Mattai et al. |
| 6,541,539 | B1 | 4/2003 | Yang et al. |
| 6,592,764 | B1 | 7/2003 | Stucky et al. |
| 6,592,980 | B1 | 7/2003 | MacDougall et al. |
| 6,592,991 | B1 | 7/2003 | Weisner et al. |
| 6,730,064 | B2 | 5/2004 | Ragheb et al. |
| 6,991,802 | B1 | 1/2006 | Ahola et al. |

(Continued)

FOREIGN PATENT DOCUMENTS

EP    0872447 A1    10/1998

(Continued)

OTHER PUBLICATIONS

Kortesuo, P., "Sol-Gel Derived Silica Gel Monoliths and Microparticles as Carrier in controlled Drug Delivery in Tissue Administration", Academic Dissertation, University of Helsinki, 2001, pp. 1-41.

(Continued)

*Primary Examiner* — Carlos Azpuru

(57) ABSTRACT

Sustained-release drug-delivery devices employing a mesoporous oxide coating that functions as a drug reservoir, and the use of mesoporous oxide coatings for improved adhesion of organic polymers to inorganic substrates.

19 Claims, 6 Drawing Sheets

U.S. PATENT DOCUMENTS

| 2002/0164380 A1 | 11/2002 | Ma et al. |
| 2008/0234810 A1 | 9/2008 | Carlson et al. |

FOREIGN PATENT DOCUMENTS

| WO | 98/34723 A2 | 8/1998 |
| WO | 99/36357 A1 | 7/1999 |
| WO | 99/47570 A1 | 9/1999 |
| WO | 00/66190 A1 | 4/2000 |
| WO | 00/25841 A1 | 5/2000 |
| WO | 00/29501 A1 | 5/2000 |
| WO | 01/28529 A1 | 4/2001 |
| WO | 02/058775 A2 | 8/2002 |
| WO | 03/055534 A1 | 7/2003 |
| WO | 2005/000740 A2 | 1/2005 |

OTHER PUBLICATIONS

Beck JS, et al., "A new family of mesoporous molecular sieves prepared with liquid crystal templates." J. Am. Chem. Soc, 1992, 114:10834-10843.

Brinker CJ, et al., "Evaporation-induced self-assembly: nanostrucutres made easy." Advanced Materials, 1999, 11 (7):579-585.

Kresge CT, et al., "Ordered mesoporous molecular sieves synthesized by a liquid crystal template mechanism." Nature, Oct. 1992, 359:710-712.

Vallet-Regi M, et al., "A new property of MCM-41: drug delivery system." Chem. Mater., 2001, 13:308-311.

Munoz B, et al., "MCM-41 organic modification as drug delivery rate regulator." Chem. Mater., 2003, 15:500-503.

Schmidt-Winkel P, et al., "Microemulsion templating of siliceous mesostructured cellular foams with well-defined ultralarge mesopores." Chem. Mater., 2000, 12:686-696.

Khushalani D, et al., "Metamorphic materials: restructuring siliceous mesoporous materials." Advanced Materials, 1995, 7:842-846.

Galarneau A, et al., "Microporosity and connections between pores in SBA-15 mesotructured silicas as a function of the temperature of synthesis." New J. Chem., 2003, 27:73-79.

Xia Y, et al., "Soft lithography." Angew. Chem. Intl. Ed., 1998, 37:550-575.

Trau M, et al., "Miroscopic patterning of orientated mesoscopic silica through guided growth." Nature, 1997, 390:674-676.

Holland BT, et al., "Synthesis of macroporous minerals with highly ordered three-dimensional arrays of spheroidal voids." Science, 1998, 281:538-540.

Imhof A, et al., "Ordered macroporous materials by emulsion templating." Nature, 1997, 389:948-951.

Yang P, et al., "Hierarchically ordered oxides." Science, 1998, 282:2244-6.

Schuth, In: Studies in Surface Science and Catalysis, Galarneau A, et al (eds.), Proceedings of the 13th Internatlional Zeolite Conference, Montpellier, France, 2001, 135:1-12.

Doadrio AL, et al., "Mesoporous SBA-15 HPLC evaluation for controlled genamicin drug delivery." Journal of Controlled Release, 2004, 97(1):125-132.

Mal NK, et al., "Photocontrolled reversible release of guest molecules from coumarin-modified mesoporous silica." Nature, Jan. 2003, 242:350-353.

Axel DI, et al., "Paclitaxel inhibits arterial smooth muscle proliferation and migration in vitro and in vivo using local drug delivery." Circulation, 1997, 96:636-645.

Drachman DE, et al., "Neointimal thickening after stent delivery of paclitaxel: change in composition and arrest of growth over six months." J. Am. Coll. Cardiol., 2000, 36:2325-2332.

Grube E, et al., "High-dose 7-hexanoyltaxol-eluting stent with polymer sleeves for coronary revascularization: one-year results from the SCORE randomized trial." J. Am. Coll. Cardiol., 2004, 44:1368-72.

Kortesuo P, "Sol-gel-processed sintered silica xerogel as a carrier in controlled drug delivery." Journal of Biomedical Materials Research, 1999, 44:162-7.

Heldman AW, et al., "Paclitaxel stent coating inhibits neointimal hyperplasia at 4 weeks in a porcine model of coronary restenosis." Circulation, 2001, 103:2289-2295.

Dauskardt RH, et al., "Adhesion and debonding of multi-layer thin film structures." Engineering Fracture Mechanics, 1998, 61:141-162.

DRUG DELIVERY SYSTEMS USING MESOPOROUS OXIDE FILMS

FIELD OF THE INVENTION

This invention is related to the field of self-assembled mesoporous template-assisted inorganic oxide films. Specifically the invention relates to the use of such films in drug delivery devices, and also the use of such films to improve adhesion between organic polymer layers and inorganic substrates.

BACKGROUND

Mesoporous Materials: Structure and Fabrication

Inorganic porous substances are classified by pore size. Those having pore sizes smaller than 2 nm are classified as microporous substances, between 2 and 50 nm are classified as mesoporous substances and larger than 50 nm are classified as macroporous substances. Porous inorganic materials are generally fabricated using a "sol-gel" process. Other methods used to fabricate porous solids include electrochemical methods and acid etching. A sol is a liquid solution containing a soluble precursor of the inorganic material of interest dissolved in an appropriate solvent. The most widely used family of sol-gel precursors are the alkoxides, compounds containing metal atoms linked to organic ligands via oxygen bridges, such as tetraethoxysilane, $Si(-OCH_2CH_3)_4$ (TEOS), a precursor of silicon dioxide (silica). Alkoxides are popular because they are easily hydrolyzed by water, either partially or fully, according to the reactions:

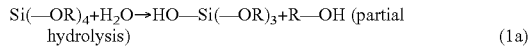

$$Si(-OR)_4 + H_2O \rightarrow HO-Si(-OR)_3 + R-OH \text{ (partial hydrolysis)} \quad (1a)$$

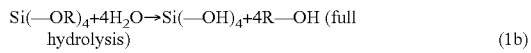

$$Si(-OR)_4 + 4H_2O \rightarrow Si(-OH)_4 + 4R-OH \text{ (full hydrolysis)} \quad (1b)$$

Two partially or fully hydrolyzed precursor molecules can undergo a condensation reaction, whereupon two silanol groups (Si—OH) are replaced by a covalent bond that involves formation of a siloxane (Si—O—Si) bridge, according to the reaction:

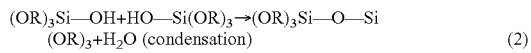

$$(OR)_3Si-OH + HO-Si(OR)_3 \rightarrow (OR)_3Si-O-Si(OR)_3 + H_2O \text{ (condensation)} \quad (2)$$

Condensation reactions between hydrolyzed precursor molecules can continue indefinitely, resulting in larger and larger structures (particles, branched chains, linear chains, etc) in the sol. The morphology, size and growth rate of these species depend on the kinetics of the hydrolysis and condensation reactions, which in turn are determined by parameters such as number of hydrolysable ligands per precursor monomer, solution concentration, amount of water or presence of a catalyst or a surfactant, temperature, pH, agitation, etc. Given enough time, condensation reactions will lead to aggregation of the growing particles or chains and, eventually, a gel will form. A gel can be visualized as a very large number of cross-linked precursor monomers forming a continuous, macroscopic-scale, solid phase, which encloses a continuous liquid phase consisting of the remaining solution. In the final steps of the sol-gel process, the enclosed solvent is removed (generally by drying) and the precursor molecules cross-link (aging) resulting in the desired inorganic solid.

Sol-gel synthesis offers several advantages over other synthetic routes for the formation of mesoporous oxides. These include mild processing conditions (low temperature, low pressure, mild pH), inexpensive raw materials, no need for vacuum processing or other expensive equipment, and a high level of control over the resulting morphology and microstructure, particularly as it pertains to porosity. Regarding shape of the finalized product, there is essentially no limitation, since the liquid sol can be cast in any conceivable form before allowed to gel, including monoliths, thin films, fibers and micro- or nano-scale particles. Porosity can be controlled via an extensive number of different methods discussed later. At the most basic level, these methods can be classified according to whether or not additional chemicals are employed as sacrificial porogens/templates.

In the simplest sol-gel process no special porogen is added to the sol and the porosity of the final solid is determined by the amount of precursor branching or aggregation (via nucleation and growth mechanisms) before gelling. Such a porous solid phase is termed a xerogel. Average pore size, volume and surface area will increase with the size of precursor species prior to deposition. In one example, silica thin films deposited via dip-coating from a sol of neutral acidity (pH 7) were shown to be aggregates of dense particles with ~100 nm radius and 65% overall pore volume (C. J. Brinker et al, in Ultrastructure Processing of Advanced Ceramics, eds. J. D. Mackenzie and D. R. Ulrich, p. 223). A problematic issue regarding xerogel synthesis is the high capillary pressures present at the final stages of solvent removal, when the liquid-air menisci recede in the small voids between the aggregating particles. These pressures can lead to substantial collapse of the porosity. For this reason, extraction of the solvent under controlled pressure/temperature conditions (a process termed supercritical extraction) is often employed, in which case the resulting porous solid is termed an aerogel. Historically, xerogels and aerogels have been the focus of the large majority of efforts to create porous sol-gel inorganic solids. For the reasons summarized above, the processes are slow, complex, and offer only a limited level of control over the resulting porous microstructure.

The incorporation of sacrificial porogens in the sol, particularly in organic (carbon-based) polymers that can be easily removed via thermolysis at elevated temperatures, is generally viewed as a more efficient method to obtain porous inorganic solids via the sol-gel synthetic route. To date, efforts have generally focused upon the fabrication of low dielectric constant (low-k) insulating films for the microelectronics industry. The most intensely studied sol-gel material for such applications is methyl silsesquioxane (MSSQ, chemical formula $MeSiO_{3/2}$), obtained by using a special alkoxide precursor with some of the hydrolysable groups replaced by non-hydrolysable alkyl ligands [e.g. dimethyldiethoxysilane $(CH_3-)_2Si(-OCH_2CH_3)_2$]. A large variety of organic porogens has been proposed as a means to template porosity in sol-gel silica, MSSQ and other sol-gel derived solids. These include, among others, star-shaped and hyperbranched poly($\epsilon$-caprolactone), poly(alkylene ether) homo- and copolymers (random, diblock and triblock including the Pluronic™ family), short-chain surfactants such as cetyltrimethylammonium bromide (CTAB), vinyl addition copolymers derived from vinyl pyridine, N,N-dimethyl acrylamide, aminoalkyl methacrylates, linear copolymers by copolymerization of methyl methacrylate and N,N-dimethylaminoethyl methacrylate, polyimides, poly(phenylquinoxalines) and poly(methylstyrene).

Importantly, porogen-based sol-gel synthesis can be achieved using a sacrificial template. The sacrificial template is an amphiphilic molecule capable of self-assembling in solution. This creates a highly-ordered liquid-crystalline (LC) nm-scale structure that guides the precursor molecules to co-assemble around the structure. Porous sol-gel inorganic solids obtained via such self-assembling templates are often referred to as mesoporous sieves and have been shown to exhibit remarkable structural properties. These include mesoscopic pore sizes, narrow pore size distributions, highly-ordered pore channel networks, mechanically robust pore walls, and extremely high surface areas (1000 $m^2/g$ or higher). Of particular importance is the case where the template assumes a cubic liquid-crystalline (LC) structure, because these lead to surface-accessible, highly-interconnected, continuous pore channel networks.

The unique properties of self-assembling template-assisted, sol-gel inorganic mesoporous materials has motivated much research effort over the last decade. In 1992, a group of researchers at Mobil Oil Corporation discovered the surfactant molecules would self-assemble in an aqueous solution of soluble silica, and upon solidification of the silica substrate, the surfactant could be removed leaving a mesoporous material ("MCM-41") having a hexagonal honeycombed array of uniform mesopores (see U.S. Pat. Nos. 5,057,296 and 5,102,643, which are fully incorporated by reference). MCM-41 is synthesized using the cationic type surfactant, quaternary alkyltrimethylammonium salts and various silica sources, such as sodium silicates, tetraethyl orthosilicate, or silica gel, under hydrothermal conditions (Beck et. al., 1992, J. Am. Chem. Soc. 114, 10834). The pore size of MCM-41 can be adjusted from about 1.6 nm up to about 10 nm by using different surfactants or altering synthesis conditions.

A variety of other self-assembling template-assisted mesoporous inorganic oxide materials are described in a number of patents. U.S. Pat. No. 6,592,991 describes block copolymers as templates for structured organic-inorganic hybrid materials. U.S. Pat. Nos. 6,592,980 and 6,365,266 describe mesoporous films having reduced dielectric constants. U.S. Pat. No. 6,592,764 describes inorganic oxide materials. U.S. Pat. No. 6,541,539 describes porous oxides. U.S. Pat. No. 6,458,310 describes a process of making a polymeric material having a microporous matrix. U.S. Pat. No. 6,334,988 describes mesoporous silicates. U.S. Pat. No. 6,054,111 describes amphiphilic block copolymers as templates for the preparation of mesoporous solids. U.S. Pat. No. 5,622,684 describes porous inorganic oxide materials prepared by non-ionic surfactant templating.

Template-assisted mesoporous materials are fabricated using two broad classes of self-assembling amphiphilic templates: short molecules (often referred to as "surfactants") and triblock copolymers. Surfactant-based methods are well described by Brinker et al. (Advanced materials 1999, 11 No. 7) and by Kresge et al. (Nature Vol 359 22 Oct 1992). The triblock copolymer template-based process (most relevant to the current invention) is described in US Patent No. 6,592,764 (fully incorporated by reference).

Mesoporous Materials used for Drug-Delivery

A number of scientific papers and patent documents refer to the use of mesoporous materials in medical or drug-related applications.

Vallet-Regi et al. (Chem. Mater. 2001, 13, 308-311) describe a powdered mesoporous material (MCM-41) that was charged with ibuprofen. Two mesoporous materials were used in this experiment each made using the surfactant templating method, and each with a different pore size (2.5 nm and 1.8 nm). But both appeared to absorb drug to the same degree and the weight percent ratio of drug to MCM-41 was 30% in both cases. The drug was shown to be released fairly steadily over a period of about 80 hours. In this case, the drug was loaded into MCM-41 by dissolving the drug in hexane and adding the MCM-41 compound to the hexane in a powdered form. Valelet-Regi et al. does not show or suggest that MCM-41 could be used to coat a surface and that a drug could then be loaded into the mesoporous coating.

Doadrio et al. (J. Controlled Release, 1997, 2004, 125-132) describe the use of HPLC techniques to measure the drug release characteristics of a mesoporous oxide (SBA-15) loaded with the antibiotic gentamicin. Gentamicin was loaded into SBA-15 by mixing SBA-15 powder to a saturated solution of drug over a period of three days. The material was then pressed into a disc, and both the disc and the drug-loaded powder were immersed into a simulated body fluid and drug release rates into the fluid were measured using HPLC.

Galarneau et al. (New J. Chem. 2003, 27:73-39) describes the microscopic and sub-microscopic structure of SBA-15. This paper details the structures of two distinct morphological forms of SBA-15—one having a synthesis temperature above 80° C. and one having a synthesis temperature below 80° C. When synthesized below 80° C. SBA-15 possesses mesopores with a diameter of about 5 nm and "ultramicropores" with a diameter <1 nm. When synthesized above 80° C. SBA-15 possesses mesopores with a diameter >9 mm and no "ultramicropores".

Mal et al. (Nature Vol 421, 23 Jan 2003, 350-353) describe a method of controlling the absorption and release of a drug, coumarin, from the pore outlets of a mesoporous silica oxide, MCM-41, using photo-activated dimerization of coumarin derivatives. The mesoporous material was made using the surfactant templating method. In this experiment, the authors emphasize that successful absorption and release depends upon the MCM-41 material being filled with molecules of the template material that caused pore formation, and also upon the "one-dimensional, isolated nature of the individual pores . . . " of the material. Mal et al. do not show a tri-block copolymer-derived mesoporous material with continuously interconnected channels that could be applied to a surface for use as a drug reservoir.

Munoz et al. (Chem. Mater. 2003, 15 500-503) describes an experiment which demonstrated that drug (ibuprofen) was delivered at a different rate from two different formulations of MCM-41, one made using a 16 carbon surfactant and one using a 12 carbon surfactant. As for the Valelet-Regi et al. paper, above, the drug was loaded into MCM-41 by dissolving the drug in hexane and adding the MCM-41 compound to the hexane in a powdered form. Munoz et al. do not show a tri-block copolymer-derived mesoporous material with continuously interconnected channels. The experiment does not show or suggest that MCM-41 could be used to coat a surface and that a drug could then be loaded into the mesoporous coating.

A number of other publications that may be relevant include the following.

WO0025841 describes a stent with a nonporous aluminum oxide coating. The coating has μm-deep, non-interconnected channels produced by electrochemical etching. The channels are oriented vertically with respect to the device surface. This stent has failed in clinical trials because the porous alumina chips or the stent surface.

WO0066190A1 discloses a porous silicon derivatized hydrosilylation that can be used in immunoisolation devices, biobattery devices, and optical devices.

U.S. Patent application publication No. 20020164380A1 describes the preparation of a mesoporous composition by adding a solvent to mixture of amphipathic compounds and alumina, then aging the mixture and purifying the product. It is suggested that these products may be useful in drug delivery vehicles.

WO9947570A1 describes the self assembly of microstructures useful in optical applications, tissue engineering and biomaterials and molecular electronic devices. p WO03055534A1 describes a fabric comprising silicon that is biocompatible and may also be able to act as an electrical conductor be used as a slow release means for drugs or fragrances, or as a collector for example for sweat.

WO9834723A2 (and EP0969922B1) describes a surface functionalized mesoporous material (SFMM) that has an ordered or organized array of functional molecules containing specific functional groups, with the functional molecules attached to the available surface area of the mesoporous substrate. The surface functionalized mesoporous material is useful for use in chemical separations.

WO0128529A1 describes a porous and/or polycrystalline silicon material used in the preparation of a pharmaceutical product for oral or rectal administration WO9936357A1 describes a mesoporous material made by forming an aqueous solution having an organometallic compound; adding a solution comprising a pore forming material selected from the group consisting of monomeric polyols, polyacids, polyamines, carbohydrates, oligopeptides, oligonucleic acids, carbonyl functional organic compounds to form a sol gel matrix by polycondensation; drying the sol gel matrix; and removing the pore forming material from the dried sol-gel matrix to thereby form a mesoporous material. The mesoporous materials have pore diameters of from about 20 angstrom to about 100 angstrom and may be used with a biologically active agent immobilized within the pores of the mesoporous material.

U.S. Pat. No. 6,511,668 (and EP0872447A1) describes a non-flaky silicon oxide powder useful as the carrier for cosmetics, drugs and perfumes.

None of these references describe a drug-delivery device comprising a triblock copolymer template-based mesoporous surface coating with substantially continuously interconnected channels designed to function as a drug reservoir. Further, none describe such a drug reservoir coating that can be made easily and inexpensively, applied evenly and consistently, and wherein a drug may be loaded into the coating after deposition onto the surface of an implantable device.

Use of Mesoporous Materials to Enhance Adhesion

Another aspect of the invention is the use of mesoporous materials to enhance adhesion between organic polymer layers and inorganic surfaces.

Interfaces between such dissimilar materials pose certain challenges for adhesion. Most inorganic solids are usually covered with a hydrophilic native surface oxide that is characterized by the presence of surface hydroxyl groups (M-OH, where M represents an atom of the inorganic material, such as silicon or aluminum). At ambient conditions, at least a monolayer of adsorbed water molecules covers the surface, forming hydrogen bonds with these hydroxyl groups. Therefore, hydrophobic organic polymers do not spontaneously wet and adhere to the surface. Furthermore, even if polymer/surface bonds (including covalent bonds) are formed under dry conditions, these bonds are susceptible to hydrolysis upon exposure to water. This effect is particularly important in applications where devices or components containing organic/inorganic interfaces must operate in aqueous, corrosive environments such as the human body.

Two different approaches are traditionally followed to reinforce organic/inorganic interfaces. The first is chemical modification of the inorganic surface via amphiphilic silane coupling agents that improve polymer wetting, bonding and interface resistance to water. The second is the introduction of controlled roughness or porosity on the inorganic surface that induces polymer mechanical interlocking.

Silane coupling agents are materials that exhibit both hydrophilic and hydrophobic behavior, and are thus termed amphiphilic. Their molecules have the general structure $Y(CH_2)_nSiX_3$, comprising a carbon chain (typically n<20), three hydrolysable groups (X) that form hydrophilic silanols (Si—OH) in solution, and a hydrophobic group (Y) selected for chemical affinity with the polymer of interest.

When a hydrophilic inorganic surface is treated with a silane solution, the hydrophilic silanols undergo condensation reactions with surface hydroxyl groups forming oxane bonds with the surface (Si—O—M). Similar to polymer/substrate bonds, silane/substrate oxane bonds are susceptible to hydrolysis but at rates several orders of magnitude lower. Siloxane bonds (Si—O—Si) also form by condensation of silanols belonging to adjacent coupling agent molecules. Additionally, the hydrophobic silane groups improve the polymer wetting of the treated surface by lowering the surface energy. Partially cross-linked coupling agent oligomers can diffuse in the polymer matrix and improve the adhesion by mechanical interlocking. If the reactivity of the hydrophobic end group is tailored to match that of the polymer, the interface can be further strengthened by co-polymerization and covalent silane/polymer bonding.

While silane groups have been used to improve adhesion between organic/inorganic interfaces and reduce hydrolysis, there remains a need for further improvements especially in aqueous, corrosive environments.

Attempts to engineer the interface morphology to improve adhesion typically focus on introducing roughness or porosity to the inorganic surface. The rough or porous surface can be created either by selective material removal from an initially flat surface or by deposition of a porous film.

Polymer wetting of the rough or porous surface results in increased contact area, so that more bonds can be established between the two materials. Furthermore, the adhesion can be improved by a change in the failure mode. A perfectly flat organic/inorganic interface will generally fail adhesively, by crack propagation along the weakest-link path in the microstructure. In contrast, rough morphology results in mechanical interlocking of the polymer and pore impregnation creates a composite phase in the interface region. Crack propagation will now likely occur by both interface adhesive and polymer cohesive failure. The latter is associated with crazing, a process in which polymer fibrils bridge the de-bond opening and connect the two mating fracture surfaces behind the crack tip. The fibrils undergo plastic deformation before rupture, dissipating energy and increasing the macroscopic interface fracture resistance.

Some attempts have been made to use nanoporous silica to improve adhesion, and Annapragada (U.S. Pat. No. 6,465,365) teaches the use of nanoporous silica films to improve the adhesion of an inorganic film and an inorganic substrate. Rutherford et al. (U.S. Pat. No. 6,318,124) teaches the use of nanporous silica on an inorganic substrate with an organic polymer coating.

In light of this background, there remains a need in the art for materials that allow improved adhesion between organic and inorganic interfaces especially in aqueous environments.

Additionally there is a need for a non-polymeric drug reservoir material that may be applied to the surface of an implantable medical device.

BRIEF DESCRIPTION OF THE INVENTION

The present invention encompasses the use of non-polymeric mesoporous oxide materials as sustained-release drug reservoirs. In certain embodiments the mesoporous oxide drug reservoir is applied as a coating to the surface of an implantable medical device to function as a drug reservoir. The present invention also encompasses drug delivery devices comprising mesoporous oxide drug reservoir, and drug delivery formulations in combination with the drug delivery reservoir of the invention. The present invention also encompasses devices and method for improved adhesion of organic polymers to inorganic substrates through the use of mesoporous films.

DETAILED DESCRIPTION

The invention encompasses non-polymeric mesoporous oxides and their uses. Specifically the mesoporous materials of the invention have properties that make them useful as: (1) controlled-release drug reservoirs, and (2) as coatings used to enhance adhesion between organic polymer layers and inorganic surfaces.

Mesoporous Oxide Materials as Controlled-Release Drug Reservoirs

The present invention encompasses a non-polymeric, inorganic, mesoporous oxide material that may be applied to the surface of an implantable medical device to function as a drug reservoir. The mesoporous drug reservoir material is made of a triblock copolymer-template-based mesoporous material having substantially continuously interconnected channels that is adapted to act as a drug reservoir capable of retaining a drug and releasing it over a defined period of time.

The mesoporous material exhibits a highly ordered surface-accessible pore channel network, substantially continuously interconnected in three dimensions throughout the entire film volume. This ordered interconnected structure allows the material to act as a drug reservoir. A drug applied to the surface of the film will penetrate the porous film, loading it with drug that is later released by diffusion, osmotic or electrochemical inducement or other means.

Figure 1:
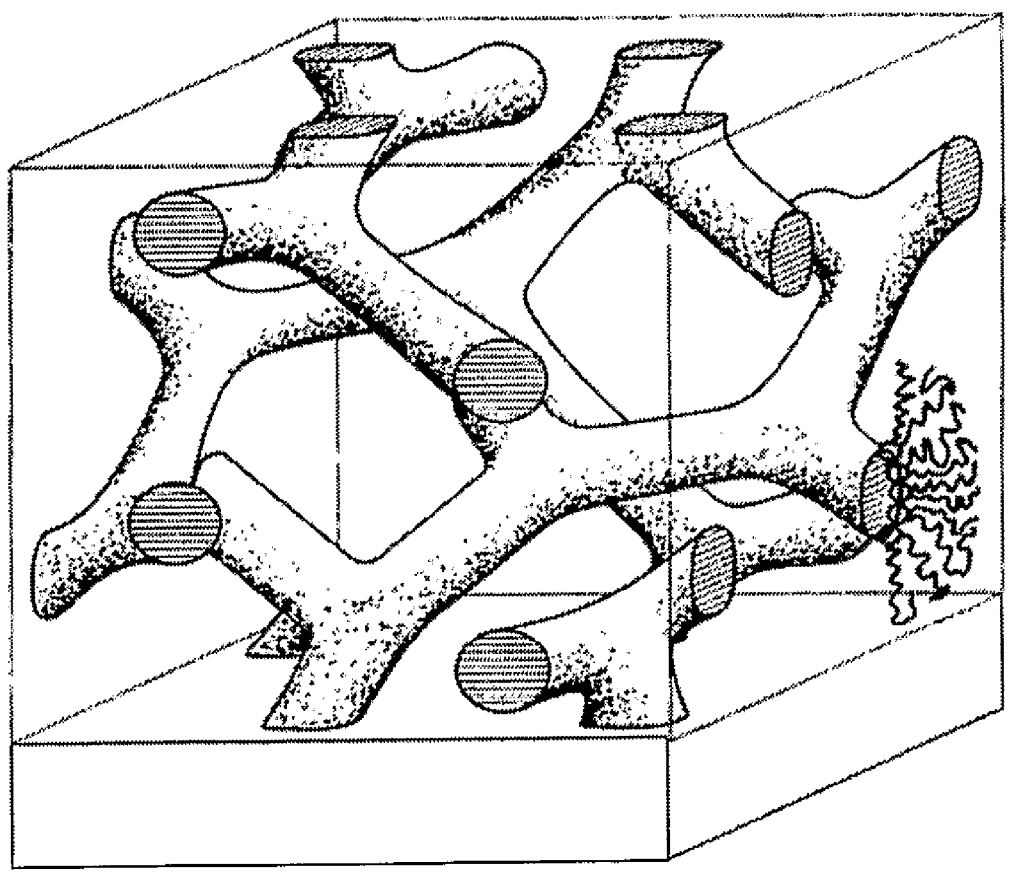
FIG. 1 shows a schematic representation of one of the various attainable mesoscopic template LC structures with cubic symmetry.

The mesoporous material of the invention is made using a triblock copolymer template that when mixed with the inorganic precursor (e.g., an alkoxide silica precursor), self-assembles into a highly-ordered 3-dimensional scaffold (FIG. 1). Thermal treatment (or room temperature exposure to a UV lamp/ozone source) removes the template and induces cross-linking of the surrounding inorganic phase into a mechanically robust network. Thus, the final material is the negative of what is shown in FIG. 1, with the block copolymer being removed to leave a network of interconnected channels. The channels so formed have predictable uniformity of size with diameters in the mesoscopic range, generally from about 2-30 nm, more usually from about 5-30 nm. Diameter of the channels can be precisely controlled via hydrothermal treatment or the addition of hydrophobic swelling agents in the initial solution, and channels may be made to have any desired diameter, for example, 2-100 nm, 3-75 nm, 5-50 nm, 7-30 nm or 10-20 nm.

The material of the present invention can be applied onto surfaces evenly and consistently by dip-coating, spray-coating, or painting, followed by removal of any excess solution material off the coated surface via flow under gravitational forces or, in the case of a stent, by rapidly rotating the device around its long axis, or by any other method known in the art. An even coat can be applied even to highly irregular surfaces, and, unlike previous mesoporous compounds, is designed such that the drug may be loaded into the coating after deposition of the mesoporous materials onto a surface of the device. Additionally, the present invention provides a mesoporous drug delivery reservoir the fabrication of which is more environmentally benign than previous drug-reservoir coatings and can be made easily and inexpensively.

The current invention may be used to provide a drug-reservoir coating on any type of implanted medical device, implanted at any location in the body of a subject. The type of device and the location of implantation will depend on the disease to be treated and the drug to be delivered. The device may be a purpose-built implantable drug delivery device for implantation sub-cutaneously or within the circulatory system. Sub-cutaneous drug delivery devices of the invention could take the form of beads, rods, discs or any other conveniently shaped device coated with the mesoporous oxide drug reservoir film of the invention and loaded with a drug. The body of the device may be made form any suitable biocompatible material such as NiTi, steel, tungsten, gold, carbon fiber, plastic etc. In a sub-cutaneous embodiment, once released from the reservoir material, the drug enters the systemic circulation and is transported to the site of action (target site). Such sub-cutaneous systemic delivery systems could be used to deliver, for example, statins, anti-psychotics, anti-arrhythmics, antibiotics, anti-retrovirals, anti-inflammatory drugs etc. Alternatively, a coated device of the invention could be implanted in close proximity to the target site. Implanting the device close to the target site is advantageous because a lower concentration of drug is required in comparison to a systemic delivery scenario, leading to lower dose requirements and lower systemic toxicity. Such local delivery systems include, for example, stents to deliver a drug to the site of insult to prevent neointimal hyperplasia, implanted beads or rods placed close to or within a tumor to deliver anti-tumor agents such as carboplatin or anti-angiogenic factors, beads to deliver anti-inflammatory drugs to the retina etc. In certain embodiments, the device is a drug-eluting stent implanted within the vasculature of a subject. In such an embodiment, the drug delivered may be an anti-restenotic drug such as a taxol-derived drug such as paclitaxel.

The invention further encompasses methods for making and using sustained-release drug delivery devices.

In other alternative embodiments, the mesoporous oxide of the invention can be used as a filter or membrane enclosing a reservoir of the biomolecules and regulating their release. For example, the bioactive molecules may be contained in microcavities or microwells etched on the surface of an implantable stent or other device, with the mesoporous layer deposited on top of the microcavity and acting as a membrane. The membrane would serve to both isolate the stored bioactive molecules underneath it from the physiologic environment and allow them to elute at a controlled rate dictated by the thickness and pore size of the membrane.

In another alternative embodiment, the mesoporous material can be used to coat particles fabricated from a material that can be degraded under chemical or thermal treatment, so that the end product would be a collection of hollow, mesoporous-shell particles (Mann et al, Chemistry of Materials, 1999, 11, p. 3021-3024). These hollow particles could be loaded with bioactive molecules, whereupon the mesoporous shell would act as a membrane regulating the elution profile. The porous, solid-core/porous-shell and hollow/porous-shell particles could further be assembled on a solid support surface or embedded in a matrix before implanted in the vicinity of the target tissue.

Drug Loading and Release Kinetics

Sustained, controlled and time-release drug delivery may be achieved using the mesoporous drug delivery reservoir (and corresponding drug delivery devices) of the invention. By varying the properties of the mesoporous material, different drug delivery release rates and profiles may be achieved for various drugs. For example, a drug may be released with approximately first order or second order kinetics. Delivery may begin upon implantation of the drug delivery device, or at a particular time after implantation, and may increase rapidly from zero to a maximal rate over a short period of time, for example less than an hour, less than 30 minutes, less than 15 minutes or less than 5 minutes. Such maximal delivery may continue for a predetermined period until the delivery rate suddenly drops. For example, delivery may continue at a maximal rate for at least 8 hours, 2 days, 4 days, 7 days, 10 days, 15 days, 30 days, 60 days or at least 90 days. On the other hand, the drug delivery rate may follow an approximately bell-shaped curve over time, with an initially slow but exponentially increasing delivery rate rising to a maximal rate and wherein the rate then exponentially decreases over time, finally tailing off to zero. In the field of sustained-release drug delivery it is generally considered desirable to avoid a drug delivery "burst" wherein the majority of the drug is delivered in a short amount of time. A desirable drug delivery profile will generally allow drug delivery at a steady rate over the pre-determined period of delivery. Any variation of delivery profile may be possible depending on what is desirable for a particular drug/disease/patient combination.

Drug loading and release properties (e.g., maximum drug loading, the rate of drug elution, and the way the elution profile changes over time) are dependant upon the properties of both the mesoporous drug reservoir and the drug formulation. Release kinetics can be altered by altering drug formulation, changing pore size of the mesoporous materials, coating the interior of the channels and by doping the material with various substances.

There are several known methods for engineering the pore size of a mesoporous sol-gel material. Pore size can be altered by altering the type of template material used and the amount used in the sol, since the size of the hydrophobic part of the amphiphilic molecule dictates to a significant degree the pore diameter. For example, the pore size of MCM-41 can be adjusted in a range of from 1.6 nm up to 10 nm (U.S. Pat. Nos. 5,057,296 and 5,102,643, and Beck et al., 1992, J. Am. Chem. Soc. 114, 10834). Another method for altering pore size is by incorporating into the sol a hydrophobic organic co-solvent that swells the hydrophobic regions after template self-assembly. The most widely used swelling agent is 1,3,5 trimethylbenzene (TMB) (P. Schmidt-Winkel et al, Chemistry of Materials, 2000, 12, p. 686-696), although in principle many other organic materials could play this role, such as triisopropylbenzene, perfluorodecalin, alkanes, alkenes, and long-chain amines (including N,N-dimethylhexadecylamine, trioctylamine, tridodecylamine). Another method involves post-synthesis hydrothermal treatment of the self-assembled gel may be used to alter pore size (D. Khushalani et al, Advanced Materials, 1995, 7, p. 842). Galarneau et al., 2003 (New J. Chem. 27:73-39) demonstrate that synthesis temperature affects the structure of the mesoporous substances formed in a binary way. When synthesized below 80° C. SBA-15 possesses mesopores with a diameter of about 5 nm and "ultramicropores" with a diameter <1 nm. When synthesized above 80° C. SBA-15 possesses mesopores with a diameter >9 mm and no ultramicropores.

Drug release kinetics can also be altered by altering the surface properties of the mesoporous channels. After completion of the sol-gel synthesis and removal of the structure-directing template, the interior surface of the pore channels can be modified to impart the desired surface functionality. The channels can be coated with a hydrophobic or a hydrophilic coating or with a charged surface coating to better interact with a drug or other substance to be carried within the mesoporous structure. One common method for doing this is by using a silane coupling agent (see Background section). Silanes can be used as linker agents to impart either a more hydrophobic or more hydrophilic property to a surface, depending on what termination moiety is used. If, for example, a carboxyl group is used as the termination molecule, then a hydrophilic property will be imparted, but if a long-chain fatty acid or a thyol is used, then a more hydrophobic property will be imparted. Various hydrophilic and hydrophobic moieties are well known in the art.

Alternatively, the channel walls can be modified by exposure to a $Cl_2$ working gas rendered reactive ($Cl_2 \rightarrow Cl^*$) by UV light, so that the channel surface becomes covered by chlorosilyl (Si—Cl) groups, which could then be further transformed to any desired functionality by processing according to the principles of organic chemistry. Similar results could be obtained via initial treatment of the pore wall surface with other working gases, including phosgene (SOCl), isocyanate (—N=C=O), malamides and others. These are chemicals that would easily react with the silanol (Si—OH) groups of the pore wall surface, thus replacing the silanols with alternative groups (e.g. Si—Cl in the case of phosgene) than can then at a subsequent step be reacted upon to impart any desired chemical functionality to the pore walls.

Another way of engineering channel properties is treatment with strong acidic or basic liquid solutions to impart surface charges. Specifically, exposure to a solution with a pH lower than the isoelectric point of the surface pI (pI=2 for silica) results in the protonation of surface silanol moieties (Si—OH→Si—$OH_2^+$), whereupon the surface becomes positively charged. Similarly, treatment with a solution of pH>pI will result in deprotonation of surface silanols and a negative net surface charge (Si—OH→Si—$O^-$). It is important to note that this charge will not be sustained upon removal from the acidic or basic solution, unless the solution also contains a charged solute of opposite sign that can attach to the charged surface via electrostatic attraction. In the latter case, the surface will remain charged and the solute attached to it even after removal form the acidic or basic solution. These properties maybe used to stimulate elution of polar or electrically charged bioactive molecules from a mesoporous matrix (discussed more below).

Different drugs have different properties. For example, heparin is the highly hydrophilic and water soluble, so a hydrophilic coating may be desirable to maximize drug loading. Paclitaxel is somewhat more hydrophobic than rapamycin, and corticosteroids are generally less hydrophobic than rapamycin or paclitaxel. If using a hydrophobic drug it would be desirable to coat the channels with a hydrophobic coating to maximize drug loading.

Drug Elution Mechanisms

A drug may be eluted in several ways. Simple diffusion may be used to release drug, in which case drug in solution will move down a concentration gradient into the environmental solution (body fluid). Osmotic effects may also be used whereby a dissolved drug may be carried by bulk fluid flow from an area of higher to lower osmotic potential. Osmotic effects may also be used to force drug from the matrix. For example, a hydrophobic drug may be forced from the matrix by filling the matrix with an increasing volume of an aqueous solution. This might be done, for example, by filling half of the mesoporous matrix with a hydrophobic drug, and partially filling the other half with a soluble salt. When implanted into a subject, water from body fluids would dissolve the salt, creating a strong osmotic potential that would draw water into the matrix. The incoming water would displace the hydrophobic drug, forcing it out of the matrix into the surrounding physiological environment. Such a system could be designed in a number of ways, and the osmotic pump could be separate from the mesoporous matrix The hydrophobicity/hydrophilicity of the interior walls of the channels of the mesoporous oxide will affect drug loading and elution. The untreated surface of mesoporous silica is hydrophilic in its natural state. If a hydrophobic drug is successfully loaded using hydrostatic pressure or otherwise, the drug will have a tendency to spontaneously elute so as to avoid contact with the hydrophilic walls. Alternatively the pore walls can be modified (as described above) to be hydrophobic, so that a hydrophilic drug would spontaneously elute. The degree of hydrophobicity of the channels can be matched with any desired drug, for example by choosing a particular termination group for a silane linker used to coat the channel walls.

Surface charge of the channel walls may be manipulated to control drug loading and elution. For example, if a negatively charged drug can be diluted in an acidic solution (pH<pI), then upon treating the surface with this solution it will become positively charged, and thus the negatively charged drug will attach to the surface due to Coulombic interactions. Blood pH=7.5>pI. Thus upon implantation, the silica surface will become negatively charged, and it will exert repulsive forces to the similarly charged drug molecules, which will spontaneously elute.

Drug release kinetics can also be adjusted by altering the physical characteristics of the drug formulation such as net charge, hydrophobicity and rheological properties of the drug formulation.

Other methods used to elute a drug from the mesoporous reservoir include the use of electrophoretic mechanisms for charged drug particles, physical gating, such as controlling the surface area of the drug reservoir exposed to the environment, and the use of various biodegradable and semi-permeable membranes that can be used to control the rate of release of a drug from the reservoir. In certain embodiments, a mesoporous oxide may be used simply as a drug reservoir, and a separate mechanism may be used to control the rate of delivery from the reservoir. For example, a membrane (e.g., a semi-permeable membrane) may be placed across the surface of the reservoir. The membrane may be designed to restrict the rate flow of a drug from the reservoir into the environment.

Drugs Suitable For Delivery Using Mesoporous Materials

The drug delivery reservoir (and corresponding drug delivery devices) of the invention may include various drugs and formulations for the treatment of various ailments.

One important aspect of the current invention is the delivery of restenosis-inhibiting drugs. Although coronary stents reduce the rate of primary restenosis compared with balloon angioplasty, 20-30% of treated vessels develop recurrent restenosis. Restenosis occurs because stent placement results in damage to the interior of the vessel. This is followed deposition of platelets and fibrin at the injured site in the coronary artery. Activated platelets express adhesion molecules such as P-selectin and glycoprotein Ib alpha, which attach to circulating leukocytes via platelet receptors such as P-selectin glycoprotein ligand. Under the influence of cytokines, leukocytes bind tightly to the leukocyte integrin (i.e., Mac-1) class of adhesion molecules via direct attachment to platelet receptors such as GP 1b alpha and through cross-linking with fibrinogen to the GP IIb/IIIa receptor. Migration of leukocytes across the platelet-fibrin layer and into the tissue is driven by chemical gradients of cytokines released from smooth muscle cells and resident leukocytes. Growth factors are released from platelets, leukocytes, and smooth muscle cells influence the proliferation and migration of smooth muscle cells from the media into the neointima. The resultant neointimal hyperplasia consists of smooth muscle cells, extracellular matrix, and macrophages recruited over several weeks.

Treatment of neointimal hyperplasia with antiproliferative drugs via coated stents to reduce neointimal hyperplasia appears very promising, and drug-eluting stents have rapidly replaced non-drug-eluting stents in standard cardio-vascular practice. Worldwide, about 1.8 million stents are implanted into patients every year, with an annual US market of about 2.2 billion dollars. Drug-eluting stents deliver drug locally, thereby requiring a lower dose of drug and minimizing systemic toxic effects. One especially effective antiproliferative drug appears to be the lipophilic drug paclitaxel (N-benzyl-beta-phenylisoserine ester, M.W. 853.9), an anti-tumor agent isolated from the bark of the yew tree. Paclitaxel is a microtubule-stabilizing drug that has been shown to inhibit vascular smooth muscle cell migration and proliferation contributing to neointimal hyperplasia (Heldman et al., Circulation. 2001 May 8: 103(18): 2289-95). Paclitaxel may be coated onto a stent by various means, such as by dip-coating by immersion in ethanolic paclitaxel and evaporation of the solvent. Per-stent dosages may rage from 1 to 1000 microgram/stent, for example 10, 50, 100, 150, 200, 250, or 500 microgram/stent, typically from about 100-300 micrograms/stent. Dosage per kilogram may be from about 0.1 to about 500 micrograms per kg, for example from 1 to 50 micrograms per kg, typically about 4-10 micrograms per kg. Inhibition of endothelial cell growth is somewhat dose-dependent, and that effective concentrations of paclitaxel range from about 0.001 to about 10 µmol/l, typically 0.01 to about 10 µmol/l (Axel et al., Circulation 1997; 96:636-645). Various sustained-release formulations and drug concentrations have been used with drug-eluting stents, for example Drachman et al. (J Am Coll Cardiol 2000; 36:2325-2332) has demonstrated that poly (lactide-co-S-caprolactone) copolymer (pLA/pCL)-coated stents containing 200 µg of paclitaxel have been shown to provide sustained paclitaxel delivery that virtually abolished rabbit neointimal hyperplasia months after stent implantation. Heldman et al. (Circulation 2001;103:2289-2295) showed that locally applied paclitaxel (bare stent with a dipcoating technique) produced a significant dose-dependent inhibition (0, 0.2, 15 and 187 µg/stent) of porcine neointimal hyperplasia at 4 weeks. Some studies have used high dosages of drug such as the study by Grube et al. (J. Am. Col. Cardiol., 44:7 2004) that used 4 to six acrylate sleeves each loaded with 800 micrograms of the paclitaxel derivative 7-hexanoyltaxol (this study proved clinically unpromising). In many papers, dosage is now given the units of mg/m$^2$, which refers to a persons body surface area, which is roughly 0.024× height$^{0.4}$× mass$^{0.5}$. Effective dosages of paclitaxel range from 50 to 200 mg/m$^2$, typically about 80, 100, and 120 mg/m$^2$.

Although ibuprofen and gentamyacin have been experimentally delivered from mesoporous oxides, it does not appear that these materials have been considered for the delivery of anti-restenotic drugs. Neither has it been suggested that mesoporous oxide materials be used for coating an implanted drug delivery device whereby the solid (not powdered) mesoporous oxide coating could be loaded with a drug after deposition on a surface of the device, and thereby used as a drug reservoir, for example with a coated stent.

Therefore, in one embodiment, the drug-delivery device is an intra-vascular device such as a stent, and the drug delivered is an agent that prevents or reduces restenosis. Such a drug may be taxol-derived lipophilic microtubular inhibitor paclitaxel. Other drugs include those that inhibit cell proliferation such as sirolimus, tacrolimus and everolimus. Other antirestenotic drugs include drugs that inhibit cell migration, e.g., batimastat, a matrix metalloproteinase inhibitor, and drugs that reduce abnormal healing e.g., estradiol. Any of these may be delivered from the drug delivery devices of the invention. Anti-angiogenic drugs such as paclitaxel, sirolimus, tacrolimus may be delivered in various doses from drug-eluting stents, as discussed above.

Any of a variety of other drugs can be delivered according the methods of the present invention. The drug delivered will vary according clinical factors. The implanted device onto which the mesoporous oxide drug reservoir is coated may be any device suitable for delivery or a particular drug. Certain devices may be implanted in the vasculature, some sub-cutaneously, some myocardially, some within a particular target organ or within a tumor. The following list of drugs is exemplary, and is not meant to be limiting in any way.

Another important family of drugs for which sustained-release delivery is desirable and that can be delivered from the mesoporous oxide reservoir of the invention is anti-inflammatory agents. These include steroids or nonsteroidal anti-inflammatory agents such as, salicylic acid derivatives (aspirin), para-aminophenol derivatives (acetaminophen), arylpropionic acids (ibuprofen), corticosteroids, and autocoid antagonists such as all histamine and bradykinin receptor antagonists, leukotriene and prostaglandin receptor antagonists, and platelet activating factor receptor antagonists. Such drugs could be incorporated into the drug reservoir of the invention in the same way as antirestenotic drugs (supra). Any form of implantable template may be used.

Antimicrobial agents that may be delivered from the mesoporous oxide of the invention include antibiotics (e.g. antibacterial), antiviral agents, antifungal agents, and anti-protozoan agents. Non-limiting examples of antimicrobial agents are sulfonamides, trimethoprim-sulfamethoxazole, quinolones, penicillins, and cephalosporins.

Also deliverable are antineoplastic agents such as doxorubicin which may be incorporated into the mesoporous oxide coating of beads or rods implanted into a tumor.

Also deliverable are angiogenic factors such as basic fibroblast growth factor (FGF), acidic fibroblast growth factor, vascular endothelial growth factor, angiogenin, transforming growth factor alpha and beta, tumor necrosis factor, angiopoietin, platelet-derived growth factor etc. These factors may be incorporated into the mesoporous oxide coating of an implantable device implanted, for example, into the myocardium of the heart to stimulate the growth of new cardiac vessels.

Calcium channel blockers that can be delivered from the mesoporous oxide reservoir include dihydropyridines such as nifedipine; benzothiazepines such as dilitazem; phenylalkylamines such as verapamil and the like.

Other useful drugs that can be delivered from the mesoporous oxide reservoir of the invention include thrombolytic agents, e.g., urokinase plasminogen activator, urokinase, streptokinase, angiotensin converting enzyme (ACE) inhibitors, spironolactone, tissue plasminogen activator (tPA) and the like. These could be coated onto a stent of other implanted device to inhibit thrombosis over a prolonged period of time.

Antihypertensive agents are another class of drug for which sustained delivery may be highly desirable and include diuretics, including thiazides; antiadrenergic agents, including clonidine and propanolol; angiotensin-converting enzyme inhibitors, including captopril; angiotensin receptor antagonists, such as losartan; and calcium channel antagonists, including nifedine. Such drugs could be incorporated into the mesoporous coating of a suitable surgical implant and implanted sub-cutaneously.

For vascular and systemic delivery, anti-coagulants include heparin; warfarin; hirudin; tick anti-coagulant peptide; and low molecular weight heparins such as enoxaparin.

Antiarrhythmic agents that can be delivered from the mesoporous oxide reservoir include sodium channel blockers (e.g., lidocaine, procainamide, encainide, flecanide, and the like), beta adrenergic blockers (e.g., propranolol), prolongers of the action potentila duration (e.g., amiodarone), and calcium channel blockers e.g., verpamil, diltiazem, nickel chloride, and the like. Such drugs could be incorporated into the mesoporous coating of a suitable surgical implant and implanted, for example, myocardially or sub-cutaneously.

Another class of drugs that can be delivered from the mesoporous oxide reservoir includes agents to treat congestive heart failure such as cardiac glycosides, an angiotensin converting enzyme inhibitors, angiotensin receptor antagonists, a nitrovasodilators, calcium channel blockers etc. Again, these could be loaded into devices implanted myocardially or sub-cutaneously.

Cholesterol lowering agents may also usefully be delivered from the mesoporous oxide reservoir and include compounds which block endogenous cholesterol biosynthesis, compounds which prevent uptake of dietary cholesterol, compounds which enhance clearance of cholesterol from the body, and the like. Exemplary cholesterol lowering agents include hypolipidemic agents e.g., nicotinic acid, probucol, etc., bile acid-binding resins e.g., cholestyramine, and fibric acid derivatives e.g., clofibrate. Other cholesterol-lowering agents include inhibitors of cholesterol biosynthesis. Examples of agents that inhibit cholesterol biosynthesis by disrupting the cholesterol biosynthetic pathway include but are not limited to HMG CoA reductase inhibitors, HMG CoA synthase inhibitors, squalene synthase inhibitors, and squalene epoxidase inhibitors. In a particular embodiment, the inhibitor of biosynthesis is a statin, e.g., lovastatin, cerivastatin, fluvastatin, pravastatin, simvaststin, etc. Long term delivery of such drugs is highly desireable.

Other drug delivery applications for which long-term sustained-release, controlled drug delivery is desirable and for which the mesoporous oxide reservoir of the invention would be useful include anti-psychotics, SSRIs, anti-seizure medication, contraceptives, systemic and local analgesics (chronic pain, bone growth/remodeling factors (osteoblast/osteoclast recruiting and stimulating factors), neurotransmitters (L-DOPA, Dopamine, neuropeptides), emphysema drugs (TGF-beta e.g. from a stent in the pulmonary artery), and drugs to combat macular degeneration (anti-angiogenesis), and small molecules such as Rapamycin (see U.S. Pat. No. 5,516,781, incorporated by reference in its entirety) or any of its derivatives. Anti-addiction drugs and opiate antagonists such as naloxone are also suitable for sustained delivery using the devices of the invention. In various embodiments of the invention sub-cutaneous implantation of a sustained release drug delivery device would be the preferred method of delivery for such drugs.

Different drugs have different properties in terms of size, hydrophobicity and charge. This will influence drug loading and release from a mesoporous drug reservoir, as explained above. For example paclitaxel, for example, is a hydrophobic (lipophilic) molecule of about 1-2 nm in size. Other hydrophobic drugs include, for example, most antipsychotics, antibiotics such as amphotericin, Dexamethasone and flutamide. Hydrophilic drugs include most hormonal peptides, antibiotics such as vancomycin, and phenobarbital, cimetidine, atenolol, aminoglycosides, hormones (e.g., thyrotropin-releasing hormone, p-nitrophenyl beta-cellopentaosideand luteinizing hormone-releasing hormone, and many others. Well known cationic include vincristine, amiloride, digoxin, morphine, procainamide, quinidine, quinine, ranitidine, triamterene, trimethoprim, vancomycin and the aminoglycosides. Anionic drugs include, for example, penicillin and many diuretics.

Use of Mesoporous Materials to Enhance Adhesion Between Organic Polymer Layers and Inorganic Surfaces The mesoporous films of the invention are very well suited for enhancing adhesion between organic polymer layers and inorganic surfaces because of the highly ordered, open, surface-accessible pore channel network that is continuously interconnected throughout the entire film volume. An organic polymer deposited on the top surface can access and penetrate the porous film through its thickness, creating a tough nanocomposite phase that extends all the way to the underlying inorganic substrate surface. Such molecular interdigitation of the polymer and the mesoporous film creates a very strong bond, resistant to corrosion and mechanical removal.

FIG. 1 shows the triblock copolymer template self-assembled into one of the various attainable liquid crystalline phases of cubic symmetry, thus forming a highly-ordered, 3-dimensional scaffold. The inorganic phase (not shown) occupies the space around the channels defined by the template. The channels have diameters in the mesoscopic range (2-30 nm) and can be precisely controlled via hydrothermal treatment or the addition of hydrophobic swelling agents in the initial solution. Diameter of the channels can be precisely controlled via hydrothermal treatment or the addition of hydrophobic swelling agents in the initial solution, and channels may be made to have any desired diameter, for example, 2-100 nm, 3-75 nm, 5-50 nm, 7-30 nm or 10-20 nm.

Figure 2:
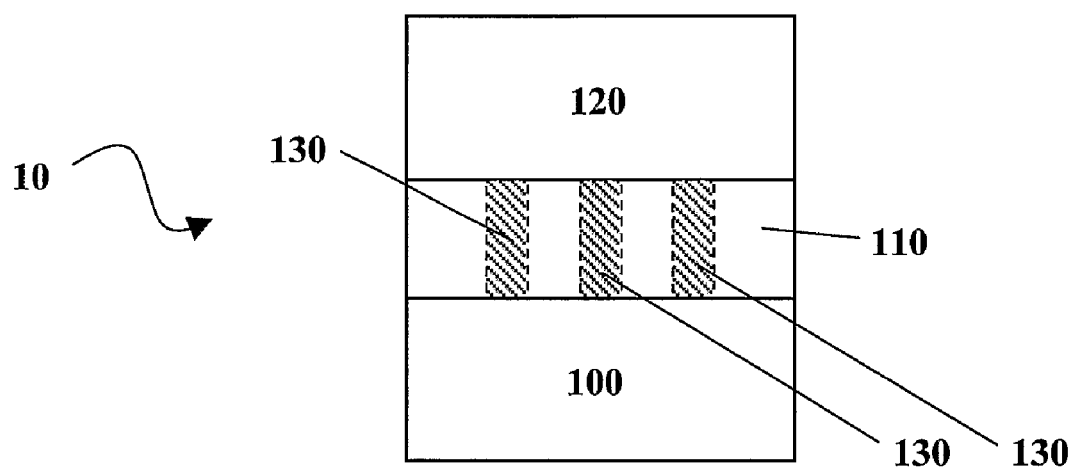
FIG. 2 shows a schematic representation of a cubic mesoporous SiO2 film on a substrate surface.

FIG. 2 illustrates the tri-layer structure 10 of the present invention used to enhance adhesion between organic polymer layers and inorganic surfaces. A mesoporous film 110 is deposited on an inorganic substrate 100. An organic polymer 120 is interdigitated through the mesoporous film 110. In a typical mesoporous film of the present invention, the average diameter of the pores 130 is between 5-30 nm and the surface density of pores (access points to the channel network) from the film top is on the order of $10^{12}/cm^2$.

Figure 3:
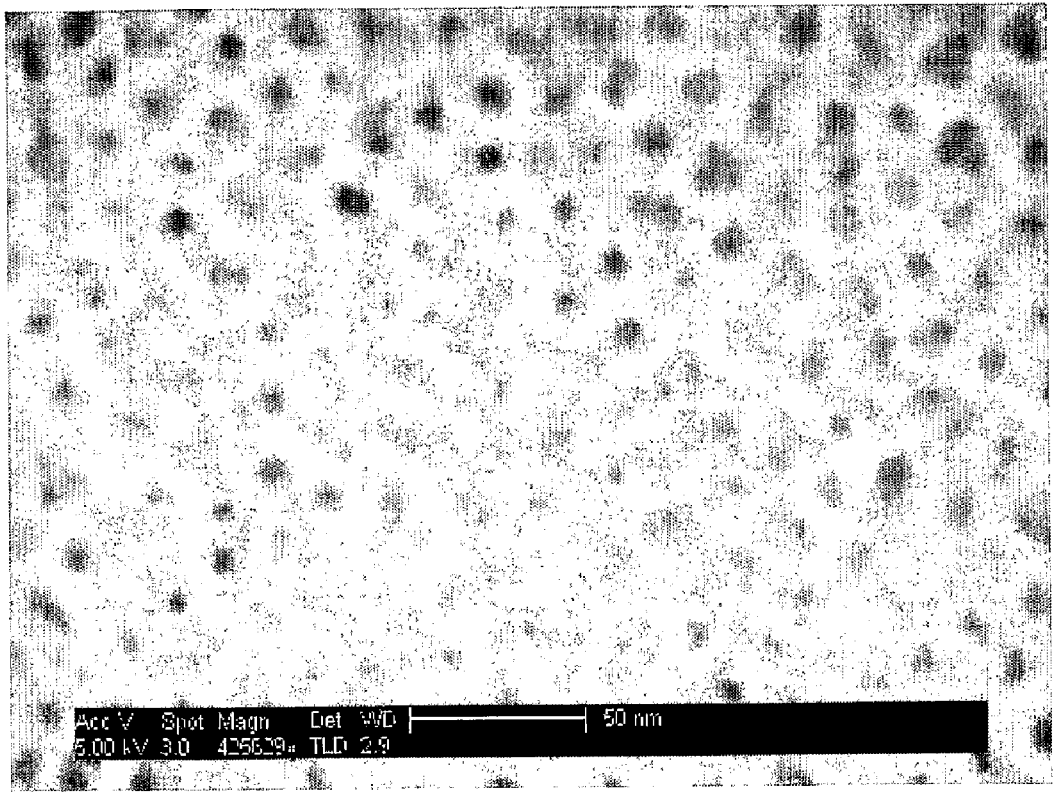
FIG. 3 shows a top-view scanning electron microscope (SEM) image of a SiO2 mesoporous film surface obtained via a triblock copolymer template.

FIG. 3 shows a top-view scanning electron microscope (SEM) image of the pores 130 in the mesoporous film 110.

Figure 4:
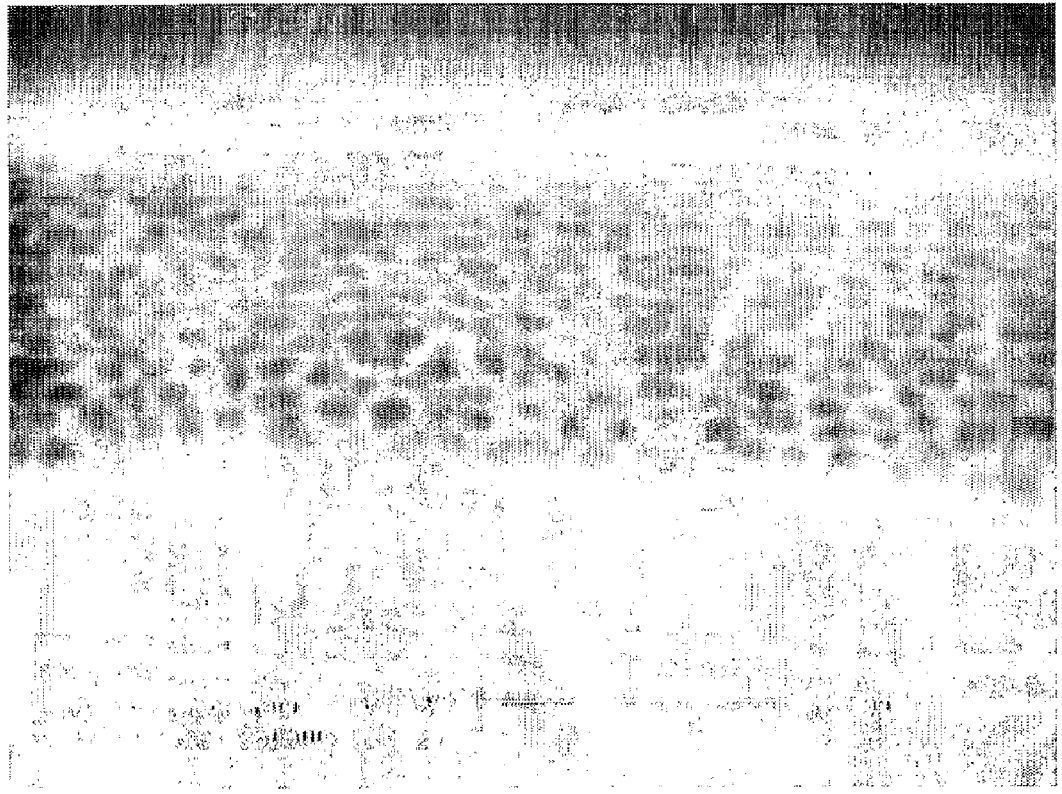
FIG. 4 shows a cross-sectional SEM image of the SiO2 mesoporous film on the surface of an inorganic substrate.

FIG. 4 shows a cross-sectional SEM image of the tri-layer structure with mesoporous film deposited on an inorganic substrate and an organic polymer interdigitated through the mesoporous film.

In using the mesoporous material of the invention to enhance adhesion, the polymer to which adhesion is sought is deposited on top of the mesoporous film by spin-coating of a precursor formulation or any other suitable method. The polymer material then enters the pores of the mesoporous film by capillary action or pressure or thermal treatment, thereby penetrating the mesoporous film substantially, preferably through its entire thickness. This penetration is followed by cross-linking of the polymer via thermal curing, by photo-controlled reaction or suitable method. Optionally, this step can be accompanied or followed by formation of covalent or other chemical bonds between the organic polymer 120 and the modified walls of the pores 130 and the surface of the inorganic substrate 100 so as to further improve the adhesion.

Production and Deposition Mesoporous Films for Adhesion or Drug-Reservoir Applications Whether for the purpose of providing a drug reservoir or for enhancing adhesion, the mesoporous films of the invention may be produced and deposited onto a substrate by the following method. (1) First, a substrate is provided, for example surgical steel, nickel-titanium alloy (NiTi), a cobalt-chrome alloy (Co—Cr), a carbon-fiber material, a plastic or other suitable biocompatible material. (2) The substrate surface is cleaned of any undesired contamination. (3) The mesoporous material is produced by mixing the inorganic precursor with amphiphilic tri-block co-polymer templating agent. Typical inorganic precursors include $SiO_2$ and $TiO_2$ such as tetraethoxysilane and titanium orthopropoxide. At this stage, if desired, other solvents may be added e.g., a rheology modifier such as ethanol or the swelling agent is 1,3,5 trimethylbenzene. (4) The template-assisted mesoporous film is deposited on the surface of the substrate, generally by spin-coating, dip-coating or spray-coating or painting of the object to be coated.

Dip-coating or spray-coating can be easily used for coating objects with complex shapes and arbitrary curvature, such as a medical implants, for example the elements of a stent. The final thickness of the mesoporous film can be controlled and optimized by diluting the solution, specifically by adding more solvent (typically ethanol) to the solution, so that in the final working solution the concentration of all the ingredients is reduced by the same amount and their relative concentration and molar ratios remain constant. Film thickness can also be adjusted by changing the spin-coating or dip-coating rate, or both, as described in detail in the examples in this application. The template material that defines the channels is then removed by thermal treatment or by room-temperature exposure to a UV lamp/ozone source. This will remove the template and induce cross-linking of the surrounding inorganic phase into a mechanically robust network. UV/ozone treatment is particularly useful if the inorganic precursor is heat sensitive.

Related Embodiments

An alternative embodiment is the use of patterning techniques to template the mesoporous material at multiple length-scales. For example, coating with a sol-gel mesoporous oxide such as silica requires a hydrophilic surface with available —OH moieties that can partake in condensation reactions with the sol-gel precursor molecules. If traditional lithography, or soft lithography (Whitesides et al, Angew. Chem. Intl. Ed, 1998, 37, p. 550) or any other surface patterning method is used to strip selected surface regions of —OH functionality before deposition, the mesoporous coating will be patterned accordingly. Alternatively, the mesoporous coating can be patterned via micro-molding in capillaries (Trau et al, Nature, 1997, 390, p. 674) where a limited amount of the liquid sol can be compressed between a flexible silicone mold and the substrate surface.

Alternatively, a second sacrificial porogen can be employed to pattern the deposition of the mesoporous coating. For example, it is a well established method to create macroporous inorganic materials (100 nm<d<10 μm) by templating the sol-gel solid via commercially available or custom-synthesized latex particles, such as monodisperse polystyrene spheres with radii in the 100-500 nm range (A. Stein et al, Science, 1998, 281, p. 538-540) or phase-separated emulsions, such as oil in formamide systems (D. J. Pine et al, Nature, 1997, 389, p. 948-951). These and other related methods can be combined with the self-assembling template processes that generate the mesoscopic-scale porosity described in our invention. The end result would be hierarchically ordered inorganic solids with multi-scale porosities (Whitesides et al, Science, 1998, 282, p. 2244). Such an approach could be particularly powerful in orthopedic applications, where a macro-scale porous implant surface is desirable to allow cell migration and bone/implant integration, whereas meso-scale porosity can be exploited for local drug delivery.

Another potentially interesting embodiment is the use of mesoporous materials that are relatively easy to obtain (such as silica) as intermediate molds for patterning other inorganic solids for which no appropriate sol-gel precursor exists, including noble metals such as gold and platinum and extending all the way to even carbon-based polymers. For example, a mesoporous silica coating can be first deposited on an implantable device, followed by "casting" via a volatile precursor or liquid-based suspension of Pd or Au nanoparticles, followed by dissolution of the mesoporous silica via hydrofluoric acid treatment, thus resulting in a mesoporous noble-metal replica of the silica framework (Schuth, in Studies in Surface Science and Catalysis, v. 135, p. 1-12).

EXAMPLE I

The organic polymer 120/native-$SiO_2$/silicon inorganic substrate 100 interface was investigated. This interface was reinforced with a cubic mesoporous $SiO_2$ film 110. The organic polymer 120 employed was a glassy, thermoset material derived from the polymerization of divinylsiloxane bis-benzocyclobutene and used in various microelectronics applications. In the rest of this document, this material will be referred to as-BCB.

Polished 3 inch test grade silicon <100>inorganic substrate 100 wafers were purchased from Silicon Quest International. Vinyltriethoxysilane [$CH_2$=$CHSi(OCH_2CH_3)_3$], tetraethylorthosilicate [TEOS, $Si(OCH_2CH_3)_4$, 98%], triethylamine [$N(-CH_2CH_3)_3$], ethanol ($CH_3CH_2OH$, dehydrated, 200 proof) and triblock copolymer Pluronic $F_{127}$ {$H(OCH_2CH_2-)_{106}[-OCH(CH_3)CH_2-]_{70}(-OCH_2CH_2-)_{106}OH$} were purchased from Gelest, Arcos Organics, Fisher Scientific, Gold Shield Chemical, and Sigma Chemical respectively, and were used as received, without further purification. Hydrochloric acid (HCl) of 0.02 M molar concentration (0.02 moles/1 t) was prepared by mixing appropriate amounts of de-ionized water (DI $H_2O$) and concentrated hydrochloric acid (36% wt, 10 M) purchased from J. T. Baker. The BCB precursor was Dow Chemical Cyclotene 3022-35 {divinylsiloxane-bis-benzocyclobutene, [$C_2H_2C_6H_4CH$=$CHSi(CH_3)_2-]_2O$}.

The list of ingredients used to prepare the surfactant/silica solution, along with respective amount mixed, molecular weight, number of moles and relative molar concentration in the solution are shown in Table I.

TABLE I

Composition of solution

| Ingredient | Amount Mixed | Mol. Weight (g/mol) | Moles | Molar Ratio |
|---|---|---|---|---|
| Tetraethoxyorthosilicate | 5.2 g | 208 | 0.025 | 1 |
| Pluronic $F_{127}$ | 2.5 g | 13,388 | $1.85 \times 10^{-4}$ | $7.4 \times 10^{-3}$ |
| De-ionized Water | 2 g | 18 | 0.125 | 10 |
| 0.02 M Hydrochloric Acid | 2.5 g | — | $5 \times 10^{-5}$ | 0.002 |
| Ethanol | 60 ml | 46 | 1.055 | 42 |

The mixing recipe was:
5.2 g of TEOS, 2 g of de-ionized water (DI—$H_2O$), 2.5 g of 0.02 M HCl and 30 ml of ethanol were mixed in a glass flask and heated at 60° C. for 15 min, while stirred with a magnetic stirrer.

2.5 g of Pluronic $F_{127}$ and 30 ml of ethanol were mixed in a separate glass beaker and heated at 60° C. for 15 min, then removed from hot plate and stirred with magnetic stirrer for 15 min.

The above two solutions were then mixed together in the flask and heated at 60° C. for 15 min, while stirred with the magnetic stirrer.

Further dilution with pure ethanol allows preparation of films with variable thickness.

A combination of solution dilution and deposition via variable spin-coat rate has allowed us to obtain the cubic $SiO_2$ mesoporous film 110 on flat surface of the silicon inorganic substrate 100 wafer with film thickness in the range of 10-150 nm. Similar variation in film thickness can be obtained by combination of solution dilution and variable dip-coat rate.

Dilution was performed by mixing a measured amount of the original solution with a corresponding amount of pure ethanol. In the final solution, the concentration of all the ingredients is lowered by the same factor. Since the self-assembly mechanism relies on solvent evaporation, the mechanism is not affected by the dilution process, as long as the relative molar concentration (molar ratio) of the solutes is not altered. Generally, lower absolute concentration and higher spin-coat rates (or lower absolute concentration and lower dip-coat rates) result in lower film thickness, as characterized by ellipsometry and summarized in Table II. In the preferred embodiment, we deposited the 25 nm-thick cubic $SiO_2$ mesoporous film 110 by using the appropriate combination of dilution and spin-coat rate, as described in Table II.

Table II. Thickness of cubic mesoporous $SiO_2$ films 110 as a function of dilution and spin-coat rate.

| Vol. diluted solution / Vol. original solution | Spin-coat Rate (krpm) | Thickness (nm) |
|---|---|---|
| 1 | 4.5 | 147 ± 3 |
| 2 | 9 | 55.5 ± 1.5 |
| 4 | 9 | 24 ± 0.5 |
| 10 | 9 | 9.5 ± 0.5 |

In one example, silicon inorganic substrate 100 wafers were cleaned for 10 min in a "Piranha" solution (1:3 $H_2O_2$:$H_2SO_4$), then rinsed and spin-dried. Then 3 ml of 4:1 diluted solution was applied on the cleaned wafer surface using plastic disposable pipettes and deposited via spin-coating at a spin-rate of 9,000 rpm. The template was removed immediately after spin-coating by thermal treatment in ambient air. The temperature was incrementally raised by 1° C./min until the target temperature of 400° C. was reached, then the samples were allowed to cool off.

Next, the porous surface was treated with a 5% wt solution of vinyltriethoxysilane coupling agent in ethanol with trace amounts of triethylamine added to catalyze siloxane bond formation with the walls of the pores 130. The vinyl functionality was selected to allow co-polymerization with BCB. Ethanol, coupling agent and catalyst were first mixed in ambient air, then the wafer was immersed and the container heated at 60° C. Wafers were removed after 30 min, cleaned for 5 min in ethanol under ultrasonic vibration and blow-dried using a nitrogen gun.

After silanation the organic polymer 120 precursor was deposited via spin-coating. 3 ml of the precursor solution was applied on the cleaned wafer surface using plastic disposable pipettes and spun at 2,500 rpm. According to the manufacturer, this results in an approximately 5 μm-thick film, as confirmed by ellipsometry measurements. Two identically prepared, BCB-coated wafers were then placed face-to-face so as to form a silicon inorganic substrate 120/native-SiO$_2$/SiO$_2$ mesoporous film 110/BCB organic polymer 120/SiO$_2$ mesoporous film 110/native-SiO$_2$/silicon inorganic substrate 100 sandwich structure. The sandwich structures were then cured in a nitrogen atmosphere and under approximately 25 kPa of compressive stress provided by the weight of a 3"-diameter W cylinder put on top of them. The temperature profile was:

Ramp for 1 hr to 150° C.
Soak for 5 hrs at 150° C. to allow precursor flow through the pores 130.
Ramp for 1 hr to 250° C. (cross-linking temperature).
Soak for various time intervals (30-120 min) at 250° C. and let cool off.

As discussed below, varying the soak time at 250° C. allows the effect of organic polymer 120 plasticity on interface adhesion to be varied.

Upon removal from the nitrogen oven, the sandwich structures are diced to create test specimens that are tested for interface fracture energy G$_c$ using the 4-Point Bend experimental set-up. The theoretical background and the specifics of this technique have been described in detail in R. H. Dauskardt, M. Lane, Q. Ma, and N. Krishna, "Adhesion and debonding of multi-layer thin film structures," *Engineering Fracture Mechanics* 61 (1), 141-62 (1998). Each pair of sandwich-bonded 3" wafers provide approximately 20 fracture specimens after dicing, and the reported adhesion strength is the average of all G$_c$ values measured for specimens originating from the sandwich.

Control silicon inorganic substrate 100/native-SiO$_2$/BCB organic polymer 120/native-SiO$_2$/silicon inorganic substrate 100 samples were also prepared and tested. The native oxide surface of these wafers was cleaned and silanated and the BCB precursor was deposited and cured following the processing steps described above. In the following discussion of the characterization, the control samples will be referred to as flat-SiO$_2$/BCB, whereas the reinforced interface will be referred to as mesoporous-SiO$_2$/BCB.

Each mesoporous film 110 was characterized immediately after template removal. Film thickness was measured with a Gaertner Scientific ellipsometer equipped with a He—Ne Laser (λ=632.8 nm) at an incident angle of 70° relative to the surface normal. The pore 130 channel structure was imaged using a Hitachi Scanning Electron Microscope (SEM).

Interface adhesion can best be quantified in terms of the macroscopic interface fracture energy G$_c$, also called critical adhesion, measured in J/m$^2$ and expressed as a sum of two terms:

$$G_c = G_o + G_p \quad (1)$$

Go includes the energy required for bond rupturing and atomic-scale plasticity at the crack tip. G$_{pl}$ accounts for energy dissipation processes occurring at an extended zone surrounding the debond area. When ductile polymer layers are present, the predominant energy absorbing mechanism is plastic deformation and the dissipation zone term is substantially higher than the near-tip one. For the experimental method used in this study, G$_c$ can be obtained from the applied strain energy release rate required for interface de-bonding.

In order to study the effect of the BCB layer plasticity on adhesion, samples have been cured for variable time intervals in the range of 30-120 min at the cross-linking temperature of 250° C. The manufacturer recommends curing the material for 60 min. Longer soak times drive the polymer chain cross-linking reaction towards completion, suppressing the ability for plastic deformation. Therefore, interface adhesion is expected to decrease with increasing soak time.

Figure 5:
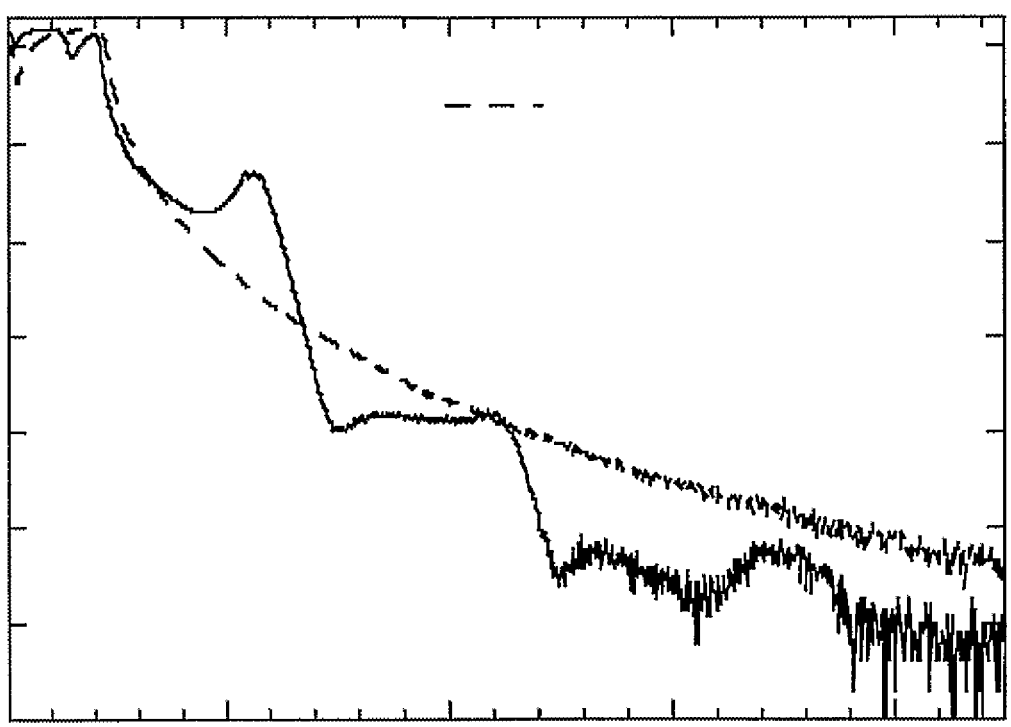
FIG. 5 shows a small angle x-ray spectrum of a mesoporous film
Figure 6:
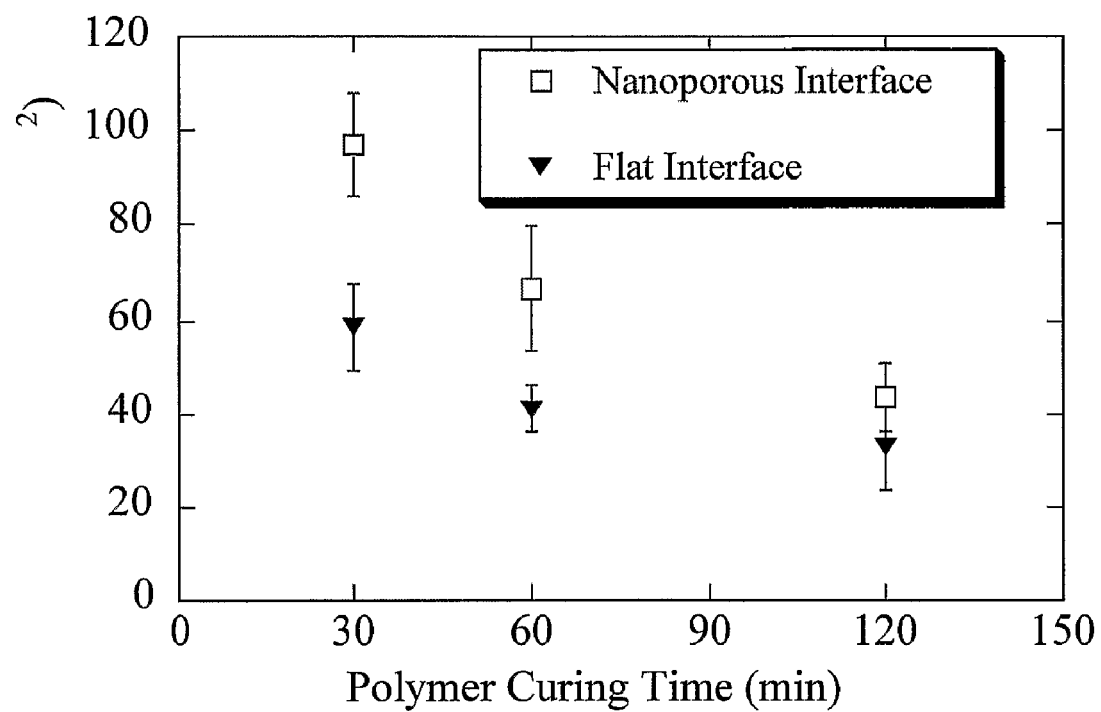
FIG. 6 is a graph showing the effect of the mesoporous film on the critical adhesion Gc as a function of polymer curing time.

Critical adhesion values for the mesoporous SiO$_2$-reinforced interface are plotted as a function of polymer curing time in FIG. 5, and compared to corresponding critical adhesion values for the flat-SiO$_2$/BCB control interface. In all cases, the porous interface significantly outperforms the control. For the 60 min cure recommended by the manufacturer, the strengthening effect is higher than 50%. As expected, the effect scales with curing time. These results, which are summarized in Table III, indicate that the present invention significantly reinforces the adhesion of organic/inorganic interfaces.

TABLE III

Experimental G$_c$ values as a function of polymer curing time for mesoporous-SiO$_2$/BCB and flat-SiO$_2$/BCB (control) interfaces.

| | Mesoporous-SiO$_2$/BCB | | Flat-SiO$_2$/BCB | |
|---|---|---|---|---|
| Curing time (min) | G$_c$ (J/m$^2$) | Std (J/m$^2$) | G$_c$ (J/m$^2$) | Std (J/m$^2$) |
| 30 | 97 | 11 | 58.5 | 9 |
| 60 | 66.5 | 13 | 41 | 5 |
| 120 | 43.5 | 7.5 | 33 | 9.5 |

There are numerous applications of the present invention. One is total hip arthroplasty. Failure of the polymethylmethacrylate (PMMA) cement/metal interface of the femoral component has been recognized as a major cause of aseptic loosening of cemented hip implants. Experimental and numerical studies have concluded that interface debonding can significantly increase the stresses in the surrounding cement mantle, leading to PMMA cracking and overall implant failure.

Several approaches have been considered to improve the reliability of the polymer/metal interface. One of the most promising has been pre-coating of the implant with a 30-50 μm-thick PMMA layer, accomplished at elevated temperatures where the lower viscosity of the polymer is expected to allow better wetting of the metal surface. This is often combined with implant surfaces roughened via a variety of methods (grit-blast finish, glass-bead finish, belt finish). The imparted morphology is designed to promote polymer interlocking and average roughness size is generally in the 0.5-15 μm range. Furthermore, it has also been demonstrated that surface treatment with silane coupling agents significantly improves the pre-coat/implant interface adhesive strength and its resistance to environmentally assisted fatigue.

However, a significant trade-off inherent in the use of rough implant surfaces has been reported. Roughness increases the polymer/metal adhesive strength but smoother implants are less abrasive and generate less debris in the event of partial interface de-bonding. Moreover, there appears to be a correlation between rougher implants and increased occurrence of bone tissue damage (osteolysis), patient pain and more immediate need for surgical revision.

The present invention is ideal for secure femoral component fixation, without sacrificing the documented advantages of polished implants. The mesoporous film material can be selected according to the implant material of choice. $SiO_2$ films can be deposited on Co—Cr—Mo, while $TiO_2$ films would likely be ideal on Ti6-A14-V components. In combination with the appropriate silane adhesion promoter, excellent bonding between the implant and the pre-coated PMMA material can be established. The superiority of this approach for adhesion over the traditional roughness imparting techniques has been discussed in the present invention. Additionally, the roughness of the surface of the mesoporous film is several orders of magnitude smaller. This characteristic should be beneficial in preventing debris generation and bone loss.

The $SiO_2$ mesoporous film deposited on Ti6-A14-V alloy substrates and exposed to simulated body fluid have been shown to induce precipitation of hydroxyapatite crystals. However, because of the pore size range, it appears unlikely that the mesoporous film would prove useful in cementless joint replacement applications, as implied in these studies. Pores with sizes in the range of 50-100 μm have been reported as the necessary minimum to allow bone tissue in-growth throughout a porous coating. In contrast, as discussed in the present invention, the mesoporous regime is ideal for accommodating polymer molecular chains.

EXAMPLE II

The oxide mesoporous film and the methods for deposition thereof described in detail in this invention provide an efficient and versatile means for successfully anchoring any organic polymer coating (the drug reservoir) to the inorganic substrate 100 of an underlying stent scaffold. Also, the mesoporous films themselves can be used to coat a stent surface and the mesoporous film can itself act as the drug-reservoir. The mesoporous film can be deposited continuously and uniformly onto an inorganic substrate, even of arbitrary complexity and topology. The process of the present invention results in a mesoporous film with a remarkably ordered pore channel network, continuously interconnected throughout the entire film volume and accessible via a dense array of surface entry points. This property is critical, because it allows loading the mesoporous film with a drug after the coating has been deposited on the stent.

The process for producing the mesoporous film for this application is similar to that already described in this invention. First, the stent surface, which is the inorganic substrate is cleaned of any undesired contamination and prepared for film deposition following any method known in the art. Then, a template-assisted, cubic mesoporous film of uniform thickness is deposited on the stent so as to cover the device surface in its entirety. This is done by first mixing the templating agent, the inorganic precursor and any other necessary ingredients in a liquid solution, preferably using an amphiphilic triblock copolymer. The chemical composition of the cubic mesoporous film is determined by the inorganic precursor of choice, can be selected to provide maximum affinity with the substrate and/or biocompatibility for clinical applications, and can be $SiO_2$, $TiO_2$ or any other appropriate composition attainable, as known in the prior art. Deposition of the solution on the stent surface is done by dip-coating or spray coating, or any other method known in the art. For example, in the dip-coating process, the device is suspended from a moving arm, lowered into a reservoir containing the liquid solution and then pulled away at a controlled speed. The exact mechanical implementation of dipping and retrieving the device from the solution reservoir may be adapted to accommodate the specifics of the stent design and so as to obtain optimum coverage of the entire surface of the device. The final thickness of the mesoporous film can be controlled and optimized by diluting the solution and/or changing the pull-out speed. After, or during, coating with the solution, the stent may be subjected to rotation around the long axis of the device, or to any other mechanical treatment as known in the art, in order to achieve a coating of uniform thickness and rid of any excess solvent material on the device. The self-assembly process takes place immediately following the coating step, and following that, the template can be removed by thermal treatment in air, or by UV irradiation in room temperature.

Optionally, the stent surface and the walls of the pores 130 of the mesoporous film 110 can be chemically modified using a silane coupling agent, or any other surface modifier that is most appropriate for improving the uptake capacity and release kinetics of the therapeutic agent of interest. The terminal species of the silane coupling agent may be chosen to produce a desired hydrophobicity or charge (discussed above). The coupling agent or surface modifier can be deposited from the liquid or, preferably, from the gas phase, by any of the methods known in the prior art.

The therapeutic agent is then incorporated in the porous network of the cubic mesoporous film via dipping the coated stent in an appropriate solution that contains the therapeutic agent or via spray-coating etc, and induced to enter the pores of the mesoporous film, via capillary action, pressure or any other method known in the art, preferably impregnating the mesoporous film in its entire thickness. After this step is complete, the device is ready for implantation.

Deposition of a mesoporous drug reservoir onto an expandable endovascular stent may be done as follows. A $SiO_2$ mesoprous film was deposited on nickel-titanium (NiTi) sample surfaces as follows: a first solution was formed by adding 3 g of the amphiphilic block-copolymer Pluronic $F_{127}$ to 10 g of ethanol in a glass beaker and heating the beaker on a hot plate at 60° C. for 20 min under vigorous stirring to fully dissolve the polymer. A second solution was formed by mixing 4 g of tetraethylorthosilicate silica precursor, 10 g of ethanol, 4 g of 0.02M hydrochloric acid and 1 g of deionized water in another glass beaker. The two solutions were then mixed together and 20 g of ethanol were added to the resulting mix. The final solution was then vigorously stirred at room temperature for 5 min, resulting in what will be referred to as the "working solution".

TiNi samples (polished ribbon pieces of approximate dimensions 0.5 cm×3 cm×250 μm) were cleaned by immersion in acetone, ethanol and isopropanol (5 min in each) under ultrasonic vibration, and then enclosed in a UV/ozone chamber for 5 min to activate the surface. Following this the samples were attached to glass slides using double-sticky 3M tape, so that only the top side would be coated while the bottom size would be masked by the glass slide. The slides were suspended from a movable arm controlled by a piezoelectric actuator, lowered into the beaker containing the working solution so that the attached samples were full immersed in the liquid, and then removed from the solution at a constant speed equal to 0.2 inches/sec.

The samples were removed from the glass slides and immediately calcined by heating at 170° C. for 15 min. so as to remove the block copolymer template and obtain mesoprous $SiO_2$ coatings on the NiTi top surface.

Various adaptations and modifications of the embodiments can be made and used without departing from the scope and spirit of the invention which can be practiced other than as specifically described herein. The above description is intended to be illustrative, and not restrictive. The scope of the invention is to be determined only by the claims.

What is claimed is:

1. A sustained-release drug delivery device comprising a structural element and a drug reservoir, wherein the drug reservoir comprises a coating applied to the surface of the structural element and wherein the coating comprises an inorganic mesoporous oxide with substantially continuously interconnected channels.

2. The sustained-release drug delivery device of claim 1 wherein the majority of the interconnected channels have a diameter of between 1-100 nm.

3. The sustained-release drug delivery device of claim 2 wherein the majority of the interconnected channels have a diameter of between 2 nm and 30 nm.

4. The sustained-release drug delivery device of claim 1 wherein the mesoporous oxide is a triblock copolymer-template-based mesoporous oxide.

5. The sustained-release drug delivery device of claim 4 wherein the mesoporous oxide is selected from the group consisting of: an oxide of silicon and an oxide of titanium.

6. The sustained-release drug delivery device of claim 1 wherein the interior surfaces of the interconnected channels are coated with an agent that modifies hydrophobicity or charge.

7. The sustained-release drug delivery device of claim 6 wherein agent that modifies hydrophobicity or charge comprises a silane coupling agent.

8. The sustained-release drug delivery device of claim 1 wherein the drug reservoir coating is applied to the surface of the structural element by a method selected from the group consisting of: dip-coating, spray coating, spin-coating and painting.

9. The sustained-release drug delivery device of claim 1 further comprising a drug loaded within the drug reservoir.

10. The sustained-release drug delivery device of claim 9 adapted for delivery of the drug for a period of at least 3 days.

11. The sustained-release drug delivery device of claim 10 adapted for delivery of the drug for a period of at least 7 days.

12. The sustained-release drug delivery device of claim 11 adapted for delivery of the drug for a period of at least 30 days.

13. The sustained-release drug delivery device of claim 9 wherein the drug is an anti-restenotic drug.

14. The sustained-release drug delivery device of claim 13 wherein the drug is a taxol-derived drug.

15. The sustained-release drug delivery device of claim 14 wherein the drug is selected from the group consisting of PACLITAXEL, SIROLIMUS, and TACROLIMUS.

16. The sustained-release drug delivery device of claim 13 wherein the drug delivery device is adapted for implantation into the vascular system of a subject.

17. The sustained-release drug delivery device of claim 16 wherein the drug delivery device comprises a stent.

18. The sustained-release drug delivery device of claim 17 wherein the total amount of drug loaded within the drug reservoir is between 1 and 1,000 micrograms per stent.

19. The sustained-release drug delivery device of claim 1 wherein the drug is selected from the group consisting of: an anti-inflammatory agent, an antimicrobial agent, and antineoplastic agent, and angiogenic agent, an anti-angiogenic agent, a thrombolytic agent, an antihypertensive agent, an anti-arrhythmic agent, a calcium channel blocker, a cholesterol-lowering agent, a psychoactive agent, an anti-depressive agent, an anti-seizure agent, a contraceptives, an analgesics, a bone growth factor, a bone remodeling factor, a neurotransmitter, and an opiate antagonist.

* * * * *